United States Patent [19]

Fadler et al.

[11] 4,038,151

[45] July 26, 1977

[54] CARD FOR USE IN AN AUTOMATED MICROBIAL DETECTION SYSTEM

[75] Inventors: Norman L. Fadler, St. Louis; Paul W. Jones; Jack R. Kirchner, both of St. Charles, all of Mo.

[73] Assignee: McDonnell Douglas Corporation, Long Beach, Calif.

[21] Appl. No.: 709,611

[22] Filed: July 29, 1976

[51] Int. Cl.$^2$ .............................................. C12K 1/10
[52] U.S. Cl. .............................. 195/127; 195/103.5 R; 195/139
[58] Field of Search ................. 195/103.5 R, 127, 139

[56] References Cited

U.S. PATENT DOCUMENTS 3,957,583   5/1976   Gibson et al. .................. 195/103.5 R

*Primary Examiner*—Raymond N. Jones
*Assistant Examiner*—Robert J. Warden
*Attorney, Agent, or Firm*—G. W. Finch; W. J. Jason; D. L. Royer

[57] ABSTRACT

Improved cards for use in an automated machine to detect the presence of specific microbes and thereby identify them, enumerate them, and/or determine their susceptibility to antibiotics. Each card includes a plate having conical detection wells each with a selected medium therein, at least one filling port with a septum which is retained by a collar formed therein, and filler passages of specific length and configuration connecting the port to the wells. Discontinuities are provided in the filler passages to prevent unwanted fluid flow and to reduce migration of the microbes when the card is in use. Overflow chambers of a specific configuration are also provided adjacent the wells to entrap bubbles.

10 Claims, 8 Drawing Figures

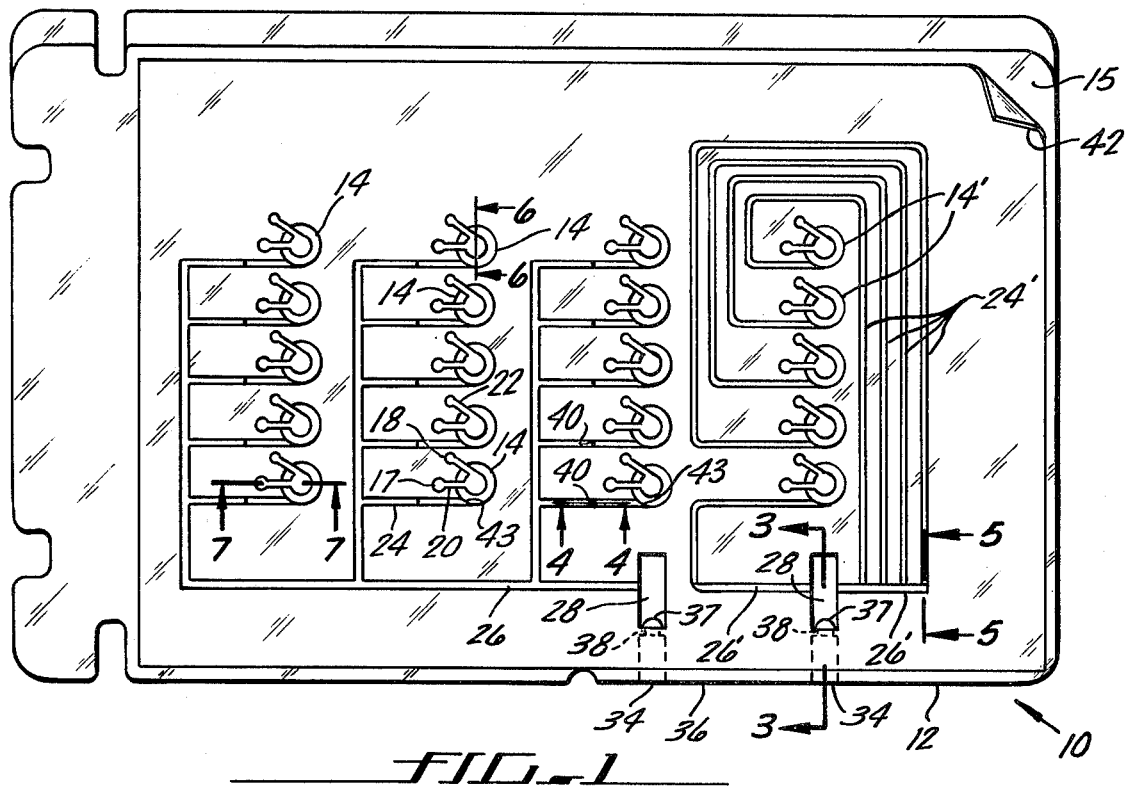
FIG_1
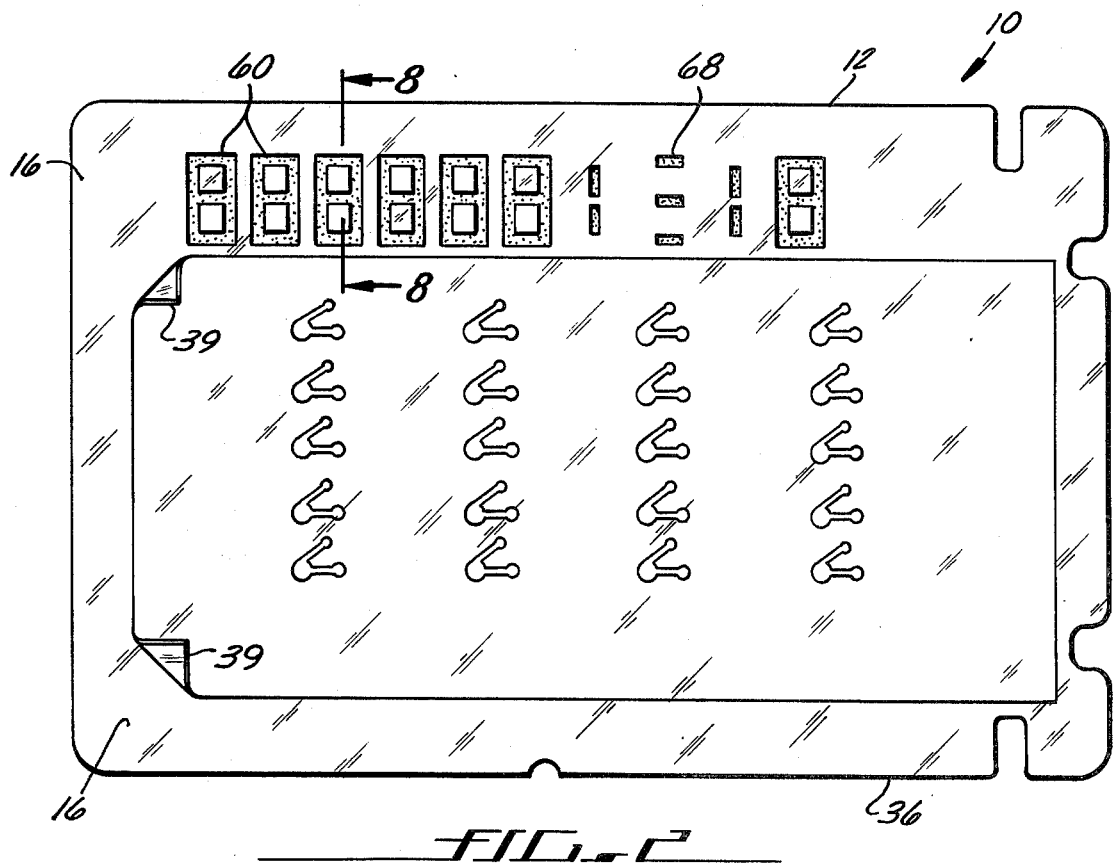
FIG_2

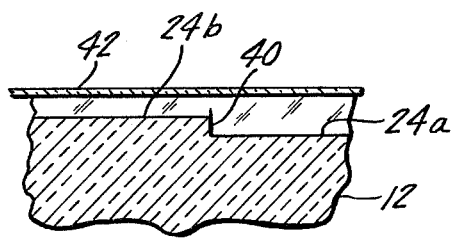
FIG._4
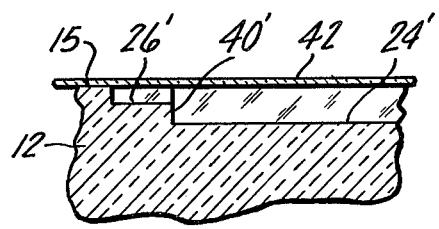
FIG._5
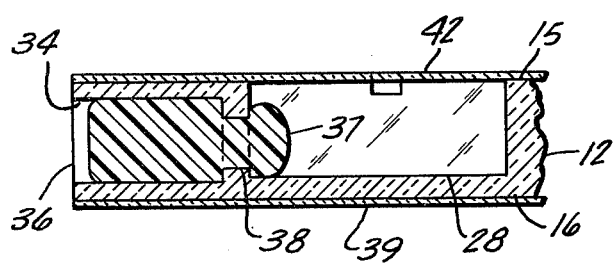
FIG._3
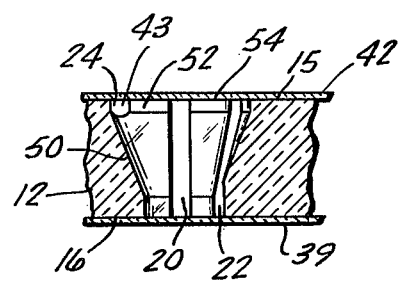
FIG._6
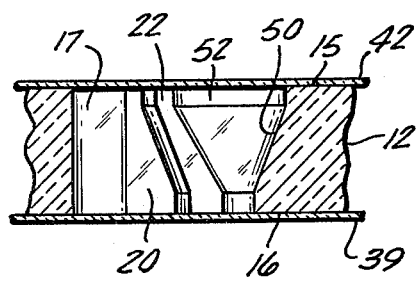
FIG._7
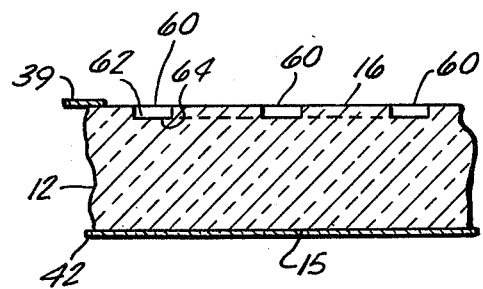
FIG._8

CARD FOR USE IN AN AUTOMATED MICROBIAL DETECTION SYSTEM

CROSS REFERENCE TO RELATED APPLICATIONS

This application covers improvements made to the cards disclosed in U.S. Patent Application, Ser. No. 647,802, entitled "Process and Apparatus for Ascertaining the Concentration of Microorganisms in a Water Specimen" by J. W. Lanham, et al, and U.S. Pat. No. 3,957,583, entitled "Apparatus and Process for Determining the Susceptibility of Microorganisms to Antibiotics" by S. F. Gibson, et al., both of which are assigned to applicants assignee. The information therein is incorporated in the specification as though fully set forth herein below.

BACKGROUND OF THE INVENTION

This invention relates in general to improvements to cards containing selective media used to determine the identity, quantity and antibiotic susceptibility of microorganisms.

There are presently existing processes and apparatus for determining the presence, identity and quantity of microorganisms and their susceptibility to antibiotics which involve placing the microorganisms into microquantities of culture media some of which will sustain specific microorganisms. The media are chemically organized so that the optical characteristics of each changes in a predetermined manner when the medium is sustaining the desired type or types of microorganisms.

A convenient way to perform these processes is through the use of a card or cassette constructed with a rigid body in the form of a plastic plate, which includes viewing chambers or wells which pass through the plate. Each of the wells is connected to a predetermined liquid specimen supply port by means of channels cut in one side of the plate. Each port includes a septum, constructed from suitable sealing compounds, which allows passage of a hollow needle when a liquid specimen is being introduced into the port.

The card is constructed by first forming the plastic plate, inserting the septum and covering one side of the plate with adhesive tape. Chosen selective media in liquid form are then placed in the proper wells and freeze dried. The opposite side of the plate is then covered with another layer of adhesive tape to form, in effect, a sealed container with at least one supply port, a plurality of wells and a piping system therebetween. Unfortunately, before the liquid media are dried, they tend to flow down the connecting grooves by means of capillary or other action and mix with the media of other chambers. This is undesirable because it can cause erroneous results when the card is used.

To introduce a specimen into the viewing wells, a vacuum is drawn through a hypodermic needle inserted through the septum at the filling port. Then atmospheric pressure is used to force the diluted liquid specimen into the card. This causes both the wells and the adjacent branches to be full of liquid containing microorganisms. When no means are provided to prevent it, the microorganisms, which are sustained by the media in the viewing wells, tend to migrate with the reconstituted media through the branches to other wells. This is undesirable because it also can cause erroneous results when the card is read. There has also been a tendency for the sealing compound which forms the septum to become dislodged during the card filling operation. This destroys the usefulness of the card.

Another problem results from the fact that some of the metabolic processes of the microbes produce gases which form bubbles in the viewing wells. Overflow chambers are normally provided adjacent the wells to provide for some bubbles such as those that result from the filling process, however, the metabolic bubbles tend to form in random fashion in the wells so that they interfere with the optical reading thereof.

SUMMARY OF THE INVENTION

The present improved card solves many of the problems discussed above by providing long passageways with discontinuities therein to prevent undesirable migration of the media before dehydration and undesirable migration of the microbes from one viewing well to another after rehydration. The wells themselves are conical in shape and include adjacent bubble chambers, which features maximumize the chances of being able to optically read the viewing well without the interference of an errant bubble. In addition, a collar is provided at the filling port to retain the septum, which extends on both sides of the collar, to assure that the port remains sealed both before and after the hypodermic needle is used to inject a diluted sample through the septum.

It is, therefore, an object of the present invention to provide an improved card for use in an automated microbial detection system.

The other object is to provide a microbe detection card having discontinuities in the liquid flow channels formed between the fill-port and the viewing wells thereof so that liquids tend to remain in a fixed position within the well and its adjacent channel.

Another object of the present invention is to provide means to prevent mixing of the media and the sustained microbes in an automated microbial detection system card.

Another object is to provide an improved viewing well in a microbial detection card which assists in overcoming the problems involved in optically reading a viewing well which may include random bubbles.

Another object is to provide means to mechanically lock an input septum in its proper position in the filling port of a microbial detection card.

These and other objects and advantages of the present invention will become apparent after considering the following detailed specification which covers a preferred embodiment thereof in conjunction with the accompanying drawings.

BRIEF DESCRIPTION OF THE DRAWINGS

FIG. 1 is a top side elevational view of the microbial detection card including the improvements of the present invention;

FIG. 2 is an underside elevational view of the card of FIG. 1 rotated 180°, about a vertical line of FIG. 1;

FIG. 3 is an enlarged cross-section of a filling port taken at line 3—3 on FIG. 1;

FIG. 4 is a greatly magnified partial cross-sectional view taken on line 4—4 of FIG. 1;

FIG. 5 is a greatly magnified cross-sectional view of a discontinuity in a channel taken at line 5—5 of FIG. 1;

FIG. 6 is an enlarged cross-sectional view of a viewing well taken at line 6—6 of FIG. 1;

FIG. 7 is an enlarged cross-sectional view of a viewing well taken at line 7—7 of FIG. 1; and FIG. 8 is an enlarged cross-sectional view taken on line 8—8 of FIG. 2.

DETAILED DESCRIPTION OF THE SHOWN EMBODIMENT

Referring to the drawings more particularly by reference numbers, number 10 in FIG. 1, designates an improved card used in a process for identifying and/or enumerating microorganisms. The card is rectangular in shape, measuring about 2½ by 3½ inches and is about ⅛ inches thick. Cards of similar size but slightly different configuration are used for antibiotic susceptibility tests.

The card 10 includes a rigid transparent plate 12, which is preferably formed from a suitable plastic such as polystyrene and is the same size and shape as the card 10. The plate 12 has a plurality of viewing wells 14 which extend completely through the plate 12 (FIGS. 6 and 7), that is from one major surface 15 to the other 16 (FIG. 2). Each well 14 defines a predetermined volume which may be virtually any desired volume depending upon the size of the card 10. In the usual case all of the wells 14 are of equal volume.

Located adjacent to each well 14 are a pair of overflow chambers, the larger one being numbered 17 and the smaller one being numbered 18. These chambers 17 and 18 extend completely through the plate 12 and hence open out of the two major surfaces 15 and 16 thereof. Each chamber, 17 or 18 is connected to its viewing well 14 through connecting passageways 20 and 22 respectively, which likewise extend between the two major surfaces 15 and 16 of the plate 12. The overflow chambers 17 and 18 assist in the complete filling of the wells 14 and in the elimination of bubbles therefrom, as will be explained in detail hereinafter.

The plate 12 further includes separate filling channels 24 leading to the viewing wells 14 from feeder channels 26, which in turn communicate with at least one filler port 28. The filling and feeder channels 24 and 26 are quite shallow with respect to the thickness of the plate 12 and open out of the major surface 15 thereof.

The filling ports 28 are relatively large and deep when compared to the filling and feeder channels 24 and 26 but the ports 28 open out of only surface 15 as can be seen by comparing FIGS. 1 and 2, with the outer ends 34 thereof enclosed by both side surfaces 15 and 16. The ends 34 open out of the edge surface 36 of the plate 12.

The complete card 12 is manufactured by first forming the plate 12 by means of a suitable mold. A rubber septum 37 is formed by insertion in plastic form through the open end 34 of the port 28. The septum 37 forms a breachable entry to seal the channels 24 and 26 and the viewing wells 14 of the card 10 from the outside atmosphere once the card is completed. An annular collar 38 is formed between the end 34 and the channel communicating portion of the port 28 to assure that the rubber septum 37 remains in the port 28. The inner diameter of the collar 38 is smaller than the rest of the port 28 and the septum 37 extends beyond both sides thereof. The septum 37 is normally constructed from a curable rubber compound which is locked securely in place by the annular collar 38 once it cures. The normally used silicon rubber liberates acetic acid as it cures. To prevent undesirable contamination, the plate 12 is then stored at suitable curing conditions long enough for the silicon rubber to stop outgassing acetic acid.

Once the septum 37 has cured, a layer 39 of transparent tape is adhesively bonded to the surface 16 of the plate 12. The type layer 39 seals what will become the bottom of the wells 14, as shown in FIG. 2. The card 10 is then oriented with respect to gravity so that the surface 16 becomes the bottom surface. Thereafter suitable culture media in liquid form are inserted in each of the viewing wells 14. Since it is undesirable that the media flow down the connecting filler and feeding channels 24 and 26 and thus mix, a discontinuity 40 is provided to interrupt any undesired flow. The discontinuity 40 is shown greatly enlarged in FIG. 4 wherein the channel portion 24a toward the filling well 14 is 20 thousandths of an inch deep and the channel portion 24b beyond the discontinuity 40 is 10 thousandths of an inch deep. The discontinuity 40 tends to restrict any media in liquid form from flowing along the channel 24. This is also assisted by the sequence of the filling process since the media is then freeze dried before a tape layer 42 similar to tape layer 39 is adhesively attached to the surface 15 of the plate 12. The use of a U-shaped channel 24 as shown in FIG. 6 rather than one completely enclosed at this point, assists in preventing capillary action from drawing the liquid media along the channel 24. The entry location 43 of the channel 24 into the well 14 is, of course, adjacent the upper surface 15 which also assists in preventing flow out from the well 14.

A similar discontinuity 40' between the wide but shallow channel 26' and the deep but narrow channel 24' is shown in FIG. 5. The channels 24' are relatively longer than the channels 24. This is because the viewing ports 14', associated therewith in the specific embodiment of the card 10 shown, are used for microbe enumeration rather than detection. Microbe mixing is much more critical in enumeration since a common medium is used in the wells 14'. The specific media in the detection wells 14 tend to protect the wells 14 from microbe migration.

When the card 10 is to be used, a hypodermic needle, not shown, is inserted through the septum 37. The hypodermic needle is connected to a supply of diluted liquid specimen containing the offensive microbes. A vacuum is then drawn through the specimen and hypodermic needle to remove the major portion of the air in the ports 28, the channels 24, 24' 26 and 26' and the viewing wells 14 and 14'. When this vacuum is released, the liquid specimen is forced into the ports, the channels and the viewing wells by atmospheric pressure. During this operation, the overflow chambers 17 and 18 are oriented upwardly from the viewing wells 14 with respect to gravity so that any residual air or bubbles tend to congregate therein. It is important that the overflow chambers 17 and 18 are connected by the passageways 20 and 22 completely along what otherwise would be the upper periphery of the viewing well 14 so that no bubbles are trapped by surface tension along the side thereof and instead the spiral flowing action of the specimen tends to scrub the walls and cause any bubbles to form in the overflow chambers where they cannot interfere with the proper operation of the viewing wells 14. The entry locations 43 of the channels 24 also are above the wells 14 and off to one side so that the incoming flow of liquid tends to follow the side surfaces 50 of the wells and scrub off adherent bubbles through a swirling action. The liquid in the specimen reconstitutes the freeze dried media in the viewing wells 14. The swirling action also assists in the reconstitution. The card 10 is then incubated with the discontinuities 40 and 40' assisting in preventing mixing of the reliquidfied media and microbe migration between adjacent viewing wells 14. The media nurture and sustain the desired offensive microbes in the specimen.

Although the overflow chambers 17 and 18 tend to eliminate bubbles due to the filling process, many microbes produce gas as a metabolic product which forms bubbles which must be accommodated if the card 10 is to be read optically. Therefore, as shown in detail in FIGS. 6 and 7, the viewing well sides 50 are generally frustro-conical in shape with a large end 52 which extends to the surface 15. The large end 52 is normally the upper surface of the card 10 when it is optically read. This causes any bubbles present in the viewing well 14 to spread out across the relatively large upper surface 54 thereof so that suitable multiple readers can look through the well 14 from enough locations that any error due to bubbles can be statistically eliminated.

The reader, which is not shown, normally is a fixed device in which the card 10 is inserted and then withdrawn. Code numbers written at predetermined locations 60 are read upon insertion of the card 10 into the reader. Slight depressions 62 as shown in FIG. 8 are used to define the proper area for the technician to write the code numbers on the card 10. Such depressions 62 may have a slightly roughened lower surface 64 to assist in the inherence of writing material. Other similar means 68 (FIG. 2) may also be included to indicate additional information. It should be noted that the tape layer 39 does not cover such means 62 and 68.

Thus, there has been shown and described an improved card for use in an automated microbial detection system which fulfils all the objects and advantages sought therefor. Many changes, alterations, modifications and other uses and applications of the subject improved card will become apparent to those skilled in the art after considering this specification together with the accompanying drawings. All such changes, alterations and modifications which do not depart from the spirit and scope of the invention are deemed to be covered by the invention which is limited only by the claims which follow.

What is claimed is:

1. In card for use in detecting the presence of microbes in a specimen wherein the card is comprised of a plate having first and second sides, detection wells for containing microbe supportive media passing from a first side to a second side therethrough, at least one filling port with a septum therein, filler passageways formed in said first side of the plate connecting said filling port to said detection wells and adhesive tape on both sides of the plate to cover said detection wells and filler passageways, the improvement comprising:

at least one discontinuity in one of said filler passageways adjacent a detection well.

2. The card defined in claim 1 wherein said filler passageways are formed in said plate have a generally U-shaped configuration whose top is covered by said adhesive tape, said filler passageway having an abrupt change in height to form said discontinuity.

3. The card defined in claim 2 wherein said filler passageway has an abrupt change in width where it has an abrupt change in height to form said discontinuity.

4. The card defined in claim 3 wherein said filler passageway has first and second portions located on opposite sides of said discontinuity, said first portion being narrower than said second portion and connecting to said detecting well.

5. The card defined in claim 2 wherein said filler passageway has first and second portions located on opposite sides of said discontinuity, said first portion being deeper than said second portion and connecting to said detecting well.

6. The card defined in claim 5 wherein said filler port has first and second port portions with an inwardly facing flange therebetween, said first port portion opening out of the edge of the plate and said second port portion opening out of the first side of said plate and a curable rubber septum positioned in said first and second port portions and being locked therein when cured by said inwardly facing flange, said open second port portion allowing escape of gases formed by the rubber curing process prior to the application of said adhesive tape to said first side.

7. The card defined in claim 5 wherein said detection wells include connected bubble chambers which extend away from said wells between said first and second sides of said plate, at least one of said wells extending away from said well in the same direction as the first portion of said filler passageway extends away therefrom.

8. The card defined in claim 7 wherein said wells are generally frustro-conical in shape having a larger diameter at said first plate side than at said second.

9. The card defined in claim 8 including indicia means in said second plate side, said indicia means including 8 shaped characters formed by generally U-shaped depressions in said second side.

10. The card defined in claim 9 wherein said U-shaped depressions have relatively rough bottom surfaces adapted to permit marking thereof, access for marking being unimpeded by said adhesive tape on said second side, said tape not extending thereover.

* * * * *